(12) United States Patent
Chen et al.

(10) Patent No.: US 11,517,601 B2
(45) Date of Patent: Dec. 6, 2022

(54) MANGOSTEEN PERICARP EXTRACT AND PROCESS FOR ITS PREPARATION THEREOF

(71) Applicant: JUNHONG BIOTECHNOLOGY CO., LTD., Taipei (TW)

(72) Inventors: Chia-Wen Chen, Taipei (TW); Rong-Hong Hsieh, Taipei (TW); Yen-Ting Chen, Taipei (TW); Yin-Jun Chen, Taipei (TW)

(73) Assignee: JUNHONG BIOTECHNOLOGY CO., LTD., Taipei (TW)

( * ) Notice: Subject to any disclaimer, the term of this patent is extended or adjusted under 35 U.S.C. 154(b) by 0 days.

(21) Appl. No.: 17/380,408

(22) Filed: Jul. 20, 2021

(65) Prior Publication Data

US 2022/0080014 A1 Mar. 17, 2022

(30) Foreign Application Priority Data

Jul. 21, 2020 (TW) .................................. 109124499

(51) Int. Cl.
| | |
|---|---|
| *A61K 36/38* | (2006.01) |
| *A61K 31/352* | (2006.01) |
| *B01D 11/02* | (2006.01) |

(52) U.S. Cl.
CPC ............ *A61K 36/38* (2013.01); *A61K 31/352* (2013.01); *B01D 11/0288* (2013.01); *A61K 2236/15* (2013.01); *A61K 2236/17* (2013.01); *A61K 2236/33* (2013.01); *A61K 2236/333* (2013.01); *A61K 2236/37* (2013.01)

(58) Field of Classification Search
None
See application file for complete search history.

(56) References Cited

U.S. PATENT DOCUMENTS 7,285,672 B2    10/2007    Sobotta et al.

FOREIGN PATENT DOCUMENTS

| CN | 102241659 A | 11/2011 |
|---|---|---|
| CN | 101525328 B | 8/2012 |
| CN | 103467433 A | 12/2013 |
| JP | WO2006137139 A1 | 1/2009 |
| TW | I627960 B | 7/2018 |

*Primary Examiner* — Michael V Meller

(74) *Attorney, Agent, or Firm* — Muncy, Geissler, Olds & Lowe, P.C.

(57) ABSTRACT

The present invention discloses a mangosteen pericarp extract and process for its preparation thereof. The mangosteen pericarp extract containing α-mangostin and γ-mangostin which obtains from preparation steps comprising fragmentation, organic solvent soaking, aqueous solution, or acidic solution soaking, concentration, spray drying and grinding steps from the rind of the mangosteen. The present invention has advantages of simple preparation process to address efficiency issue, no need to have heating under reflux in extraction steps and the solvents which used are friendly to human body and environment.

1 Claim, 1 Drawing Sheet

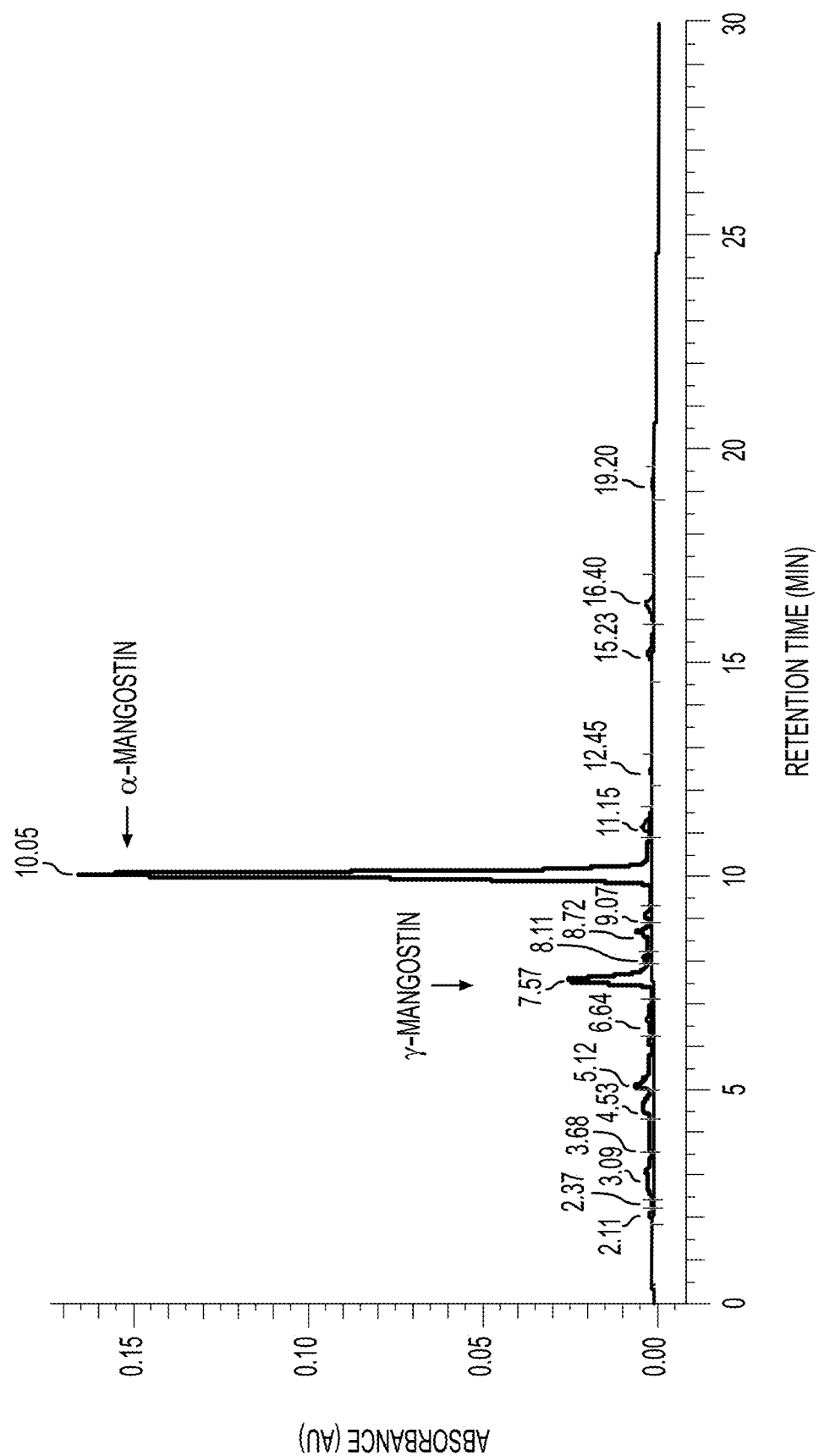

MANGOSTEEN PERICARP EXTRACT AND PROCESS FOR ITS PREPARATION THEREOF

FIELD OF THE INVENTION

The present invention is related to the technical field of mangosteen pericarp extract and process for its preparation thereof, particularly a mangosteen pericarp extract containing α-mangostin and γ-mangostin and a process for preparing the mangosteen pericarp extract.

BACKGROUND OF THE INVENTION

Some studies have shown that the rind of the mangosteen has special phytochemicals which is "Xanthone". The xanthone had be found that it has a distinct chemical structure, known as tricyclic aromatic system, which consist of two benzene rings attached through a carbonyl group (C6-C1-C6 structure) and oxygen. It has various of chemical names due to the binding of different functional groups such as hydroxyl group and isoprene. α-mangostin and γ-mangostin are two members of the class of xanthone in mangosteen pericarp which have higher proportion, and they exhibited antibacterial effect, as well as antioxidant effect caused by great chelating activity. Recent researches found that mangostin can protect pancreatic cells and lower blood sugar levels in diabetic subjects and therefore the mangosteen pericarp extracts are often used to be prepared functional food and supplements.

Currently, microwave extraction method and Soxhlet extraction method are two common methods be used for extracting xanthone from the rind of the mangosteen, and the methods need to heat organic solvent including ethyl acetate, methanol, ethanol, petroleum ether, and other aromatic compounds under reflux process due to xanthone is water-insoluble substance and to implement freeze drying or spray drying process to obtain the crude extracted product. In order to obtain higher purity extracted product, need to undergo fractional distillation or use another organic solvent including dichloromethane, petroleum ether or toluene to conduct secondary extraction. For example, U.S. Pat. No. 7,285,672 describes a process for isolating and purifying pure α-mangostin from the rind of mangosteen fruit, its step comprising: the plant material is pre-softened in water for 12-13 hours and is combined with three times the amount of toluene as extracting solvent to extract the plant material at 59 to 70° C., and then is conducting concentration and recrystallisation processes; dissolving the crude product in a mixture of 1,2-ethanediol and toluene in a ratio of about 96:4 at 80° C.; cooling to room temperature and filtering the solution; recrystallization process is carried out with ethanol/water to obtain α-mangostin. China patent NO. 103467433 discloses a method for extracting α-mangostin and the method comprising the mangosteen pericarp is pulverized and is combined with eight to ten times the amount of aqueous solution to perform one to two times reflux extraction and one to three hours for each time; using eight to ten times the amount of 90% to 95% ethanol solution to perform one to three times reflux extraction and one to three hours for each time; concentrating, isolating and drying to obtain crude product; using weight ratio 60:70 to 30:40 of dimethyl ether and butane as extracting solvent to perform subcritical fluid extraction and then to obtain high purity of α-mangostin after solvent is evaporated. China patent No. 101525328 also discloses a method using chloroform and ethyl acetate as organic solvent to obtain high purity of α-mangostin. International application No. PCT/JP2005/011502 (published as WO/2006/137139) provides a method of isolating a mangosteen derivative and the steps comprising to heat and wash mangosteen pericarp by adding water at 90° C.; to perform extraction and filtration process at 50 to 85° C. after adding concentration of 25~75% ethanol to obtain crude product; dissolving crude product with ethanol with a concentration of 25~75%; obtaining purified mangosteen derivative after recrystallization, and the purified mangosteen derivative has total amount of 90% α-mangostin and γ-mangostin and the content ratio of α-mangostin to γ-mangostin is 75~85% to 7~75%.

Conventional extraction techniques arise several problems. First, the steps are complicated and must consume energy for heating and refluxing. Second, most of methods only can generate single kind of xanthone, usually α-mangostin, and different kind and content of xanthone can not be obtained from a single preparation process. Third, need to use organic solvents with high toxicity such as dichloromethane, petroleum ether or toluene which are harmful to human body and the environment.

SUMMARY OF THE INVENTION

In view of the above problems, the present invention is directed to a mangosteen pericarp extract and process for its preparation with simple preparation steps to address efficiency issue and with advantage of having α-mangostin and γ-mangostin in the extract product from the rind of the mangosteen in the same preparation process.

To achieve the objectives, a preparation process for mangosteen pericarp extract of the present invention comprising:

drying and fragmenting the mangosteen pericarp to obtain fragment of mangosteen pericarp;

soaking the fragment of mangosteen pericarp in organic solvent with a concentration of at least 70% and placing it at room temperature, and filtering it to obtain a mangosteen pericarp organic solvent extract, wherein the ratio of the weight to volume of the fragment of mangosteen pericarp and the organic solvent is 1:5 to 1:20;

soaking and heating the fragment of mangosteen pericarp obtained from the previous step in aqueous solution and placing it at room temperature, and filtering it to obtain a mangosteen pericarp aqueous extract and a mangosteen pericarp residue, wherein the ratio of the weight to volume of the fragment of mangosteen pericarp and the aqueous solution is 1:10 to 1:20;

concentrating the mangosteen pericarp organic solvent extract and the mangosteen pericarp aqueous extract to obtain a mangosteen pericarp organic solvent concentrate and a mangosteen pericarp aqueous concentrate; and spray drying the mangosteen pericarp organic solvent concentrate to obtain a α-Xones Extract, wherein the α-Xones Extract containing 10% to 30% of xanthone.

The process mentioned above further comprising the following steps:

adding a first specific amount of the aqueous or acidic solution into the mangosteen pericarp organic solvent concentrate, homogenizing it, placing it at room temperature, and separating it into a first upper layer aqueous solution and a first lower layer precipitate;

isolating the first upper layer aqueous solution and adding a second specific amount of ethanol to dissolve the first lower layer precipitate, and obtaining a mangosteen pericarp ethanol filtrate by filtration; and spray drying the mangosteen pericarp aqueous concentrate and the first upper layer aqueous solution to obtain α-Xones Aqua Choice.

The process mentioned above further comprising the following steps:

adding alkane solvent with volume ratio is 1:1 to 1:10 into the mangosteen pericarp ethanol filtrate and mixing by vortex mixer, placing it at room temperature, and separating it into an upper layer alkane solvent and a lower layer ethanol filtrate;

heating and concentrating the lower layer ethanol filtrate in water bath to obtaining a lower layer ethanol concentrated filtrate, and adding and mixing aqueous solution with volume ratio is 1:1 to 3:1 into the lower layer ethanol concentrated filtrate, placing it at low temperature, and separating it into a second upper layer aqueous solution and a second lower layer precipitate; and fragmenting, air-lay drying and grinding the second lower layer precipitate to obtain α-Xones Prime, wherein the α-Xones Prime containing at least 50% of xanthone.

The process mentioned above further comprising the following steps:

air-lay drying and grinding the mangosteen pericarp residue to obtain α-Xones Prebio.

The organic solvent in the process mentioned above is methanol, ethanol, ethyl acetate or chloroform.

The aqueous solution in the process mentioned above is distilled water, deionized water or solutions prepared from acid salts or metal ion salts. The acidic solution is formic acid, propionic acid, hydrochloric acid, phosphoric acid, sulfuric acid, carbonic acid, acetic acid, citric acid, or oxalic acid. The α-Xones Aqua Choice containing 1% to 5% of mangosteen water-soluble polyphenol, and the mangosteen water-soluble polyphenol comprising chlorogenic acid, epicatechin and procyanidins.

The alkane solvent in the process mentioned above is in liquid form at room temperature.

To achieve the objectives, a mangosteen pericarp extract of the present invention comprising at least 10% of xanthone, wherein the xanthone containing 65% to 75% of α-mangostin and 10% to 15% of γ-mangostin.

The mangosteen pericarp extract mentioned above comprising at least 30% of xanthone.

The mangosteen pericarp extract mentioned above comprising at least 50% of xanthone.

BRIEF DESCRIPTION OF THE DRAWINGS

The FIGURE is an analysis result of ratio of α-mangostin and γ-mangostin in the extract of the present invention.

DETAILED DESCRIPTION OF THE PREFERRED EMBODIMENTS

In order to fully comprehend the objectives, features and efficacy of the present invention, a detailed description is described by the following substantial embodiments in conjunction with the accompanying drawings. The description is as below.

As used herein, the description of unit, element and component in the present invention uses "one", "a", or "an". The way mentioned above is for convenience, and for general meaning of the category of the present invention. Therefore, the description should be understood as "include one", "at least one", and include the singular and plural forms at the same time unless obvious meaning.

As used herein, the description of "comprising", "comprises", "include", "includes", "including" and other similar terms used in the present invention are meant to be non-limiting. For example, it may include any components or ingredients that are not specifically listed in the description.

The mangosteen pericarp extract preparation process of the present invention is first drying and fragmenting the mangosteen pericarp to obtain fragment of mangosteen pericarp. To facilitate subsequent extraction operations, the fragment could be divided and packaged by food grade of cotton filter bags or stainless-steel filter buckets. The fragment of mangosteen pericarp is soaked in organic solvent with certain concentration and ratio and is placed at room temperature for a while, and then to perform filtering to obtain a mangosteen pericarp organic solvent extract, wherein the certain ratio means the weight to volume of the fragment of mangosteen pericarp and the organic solvent is 1:5 to 1:20, preferably 1:5 to 1:10, and the certain concentration means volume percentage concentration is at least 70%, preferably at least 80%, more preferably at least 90%, the organic solvent including but not limit to methanol, ethanol, acetic acid, ethyl acetate and chloroform. Following soaked in organic solvent, the fragment of mangosteen pericarp is soaked in aqueous solution with certain ratio and is placed at room temperature after heating, and then is filtered to obtain a mangosteen pericarp aqueous extract and a mangosteen pericarp residue, wherein the ratio means the weight to volume of the fragment of mangosteen pericarp and the aqueous solution is 1:10 to 1:20, preferably 1:10 to 1:20. α-Xones Prebio can be obtained by spray drying at 40 to 60° C. and grinding the mangosteen pericarp residue, especially, α-Xones Prebio in the present invention refers to a mangosteen pericarp extract of its fiber. To concentrate the mangosteen pericarp organic solvent extract and the mangosteen pericarp aqueous extract to obtain a mangosteen pericarp organic solvent concentrate and a mangosteen pericarp aqueous concentrate and α-Xones Extract can be obtained by spray drying of the mangosteen pericarp organic solvent concentrate, especially, α-Xones Extract in the present invention refers to a low purity of the mangosteen pericarp extract containing 10% to 30% of xanthone.

Following the process mentioned above, the process further comprising the steps of adding amount of the aqueous or acidic solution into the mangosteen pericarp organic solvent concentrate and homogenizing, and be separated into a first upper layer aqueous solution and a first lower layer precipitate after being placed at room temperature for a while, then isolating the first upper layer aqueous solution and adding amount of ethanol to dissolve the first lower layer precipitate and be filtered to obtain a mangosteen pericarp ethanol filtrate; and α-Xones Aqua Choice can be obtained by spray drying the mangosteen pericarp aqueous solution concentrate and the first upper layer aqueous solution, wherein the weight to volume of first lower layer precipitate and ethanol is 1:1 to 1:2, preferably 1:1 to 1:1.5, especially, α-Xones Aqua Choice in the present invention refers to mangosteen pericarp water-soluble extract containing 1 to 5% of mangosteen water-soluble polyphenol including but not limit to polyphenol comprising chlorogenic acid, epicatechin and procyanidins.

Following the process mentioned above, the process further comprising the steps of adding alkane solvent with volume ratio is 1:1 to 1:10 into the mangosteen pericarp ethanol filtrate and mixing it to as suspension by vortex mixer and be separated into an upper layer alkane solvent and a lower layer ethanol filtrate after being placed at room temperature for a while, wherein the alkane solvent refers to alkanes in liquid form at room temperature, which including but not limit to N-pentane, N-hexane, and N-heptane. Next, the lower layer ethanol filtrate is isolated and heated in water bath and is concentrated at low temperature to obtain a lower layer ethanol concentrated filtrate and then to add and mix aqueous solution with volume ratio is 1:1 to 3:1 into the lower layer ethanol concentrated filtrate, and it would be separated into a second upper layer aqueous solution and a second lower layer precipitate after being placed at low temperature for a while. Then, α-Xones Prime can be obtained by fragmenting, spray drying, and grinding the second lower layer precipitate, especially, the α-Xones Prime in the present invention refers to a high purity of the mangosteen pericarp extract containing at least 50% of xanthone.

Example 1

To obtain fragment of mangosteen pericarp by drying and fragmenting the mangosteen pericarp and then the fragment is divided and packaged to a food grade of stainless-steel filter bucket. The fragment of mangosteen pericarp is soaked in ethyl acetate with the ratio of weight to volume of 1:5 and the concentration of 70% and is placed at room temperature overnight and then to perform filtering to obtain a mangosteen pericarp ethyl acetate extract. Next, the fragment of mangosteen pericarp is soaked in distilled water with ratio of weight to volume of 1:10 and is placed at room temperature overnight after heating at 95° C. for two hours; mangosteen pericarp water extract and mangosteen pericarp residue both be isolated by filter, and then α-Xones Prebio can be generated by spray drying and grinding the mangosteen pericarp residue at 40 to 60° C. Next, to concentrate the mangosteen pericarp ethyl acetate extract and the mangosteen pericarp water extract to obtain a mangosteen pericarp ethyl acetate concentrate and a mangosteen pericarp water concentrate, and then spray drying the mangosteen pericarp ethyl acetate concentrate to obtain α-Xones Extract, wherein the α-Xones Extract containing about 10% of xanthone (based on the total content of α-mangostin and γ-mangostin) and the percent yield is 40% to the initial weight of mangosteen pericarp. Moreover, to add amount of distilled water into the mangosteen pericarp ethyl acetate concentrate and it would be separated into a first upper layer aqueous solution and a first lower layer precipitate after homogenizing and being placed at room temperature for a while; then, to isolate the first upper layer aqueous solution and to add amount of ethanol with ratio of weight to volume of 1:1 to dissolve the first lower layer precipitate, and be filtered to obtain a mangosteen pericarp ethanol filtrate; and then α-Xones Aqua Choice can be obtained by spray drying the mangosteen pericarp aqueous solution concentrate and the first upper layer aqueous solution, wherein the α-Xones Aqua Choice containing about 1% of mangosteen water-soluble polyphenol and the percent yield is 20% to the initial weight of mangosteen pericarp. Moreover, N-hexane is added with volume ratio is 1:5 into the mangosteen pericarp ethanol filtrate and it would be separated into an upper layer alkane solvent and a lower layer ethanol filtrate after is mixed by vortex mixer to suspension state and being placed at room temperature for a while; the lower layer ethanol filtrate is heated in water bath at 45 to 50° C. and the is concentrated to obtaining a lower layer ethanol concentrated filtrate and then distilled water is added with volume ratio is 1:1.5 and it would be separated into a second upper layer aqueous solution and a second lower layer precipitate after mixing and being placed at 6° C. overnight; Final, to perform fragmenting, spray drying at 40° C., and grinding to obtain α-Xones Prime, wherein the α-Xones Prime containing at least 50% of xanthone (based on the total content of α-mangostin and γ-mangostin) and the percent yield is 10% to the initial weight of mangosteen pericarp.

Example 2

To obtain fragment of mangosteen pericarp by drying and fragmenting the mangosteen pericarp and then the fragment is divided and packaged to a food grade of stainless-steel filter bucket. The fragment of mangosteen pericarp is soaked in ethanol with the ratio of weight to volume of 1:20 and the concentration of 90% and is placed at room temperature overnight and then to perform filtering to obtain a mangosteen pericarp ethanol extract. Next, the fragment of mangosteen pericarp is soaked in distilled water with ratio of weight to volume of 1:10 and is placed at room temperature overnight after heating at 95° C. for two hours; mangosteen pericarp water extract and mangosteen pericarp residue both be isolated by filter, and then α-Xones Prebio can be generated by spray drying and grinding the mangosteen pericarp residue at 40 to 60° C. Next, to concentrate the mangosteen pericarp ethanol extract and the mangosteen pericarp water extract to obtain a mangosteen pericarp ethanol concentrate and a mangosteen pericarp water concentrate, and then spray drying the mangosteen pericarp ethanol concentrate to obtain α-Xones Extract, wherein the α-Xones Extract containing about 30% of xanthone (based on the total content of α-mangostin and γ-mangostin) and the percent yield is 60% to the initial weight of mangosteen pericarp. Moreover, to add amount of distilled water into the mangosteen pericarp ethanol concentrate and it would be separated into a first upper layer aqueous solution and a first lower layer precipitate after homogenizing and being placed at room temperature for a while; then, to isolate the first upper layer aqueous solution and to add amount of ethanol with ratio of weight to volume of 1:1 to dissolve the first lower layer precipitate, and be filtered to obtain a mangosteen pericarp ethanol filtrate; and then α-Xones Aqua Choice can be obtained by spray drying the mangosteen pericarp aqueous solution concentrate and the first upper layer aqueous solution, wherein the α-Xones Aqua Choice containing about 5% of mangosteen water-soluble polyphenol and the percent yield is 20% to the initial weight of mangosteen pericarp. Moreover, N-hexane is added with volume ratio is 1:5 into the mangosteen pericarp ethanol filtrate and it would be separated into an upper layer alkane solvent and a lower layer ethanol filtrate after is mixed by vortex mixer to suspension state and being placed at room temperature for a while; the lower layer ethanol filtrate is heated in water bath at 45 to 50° C. and the is concentrated to obtaining a lower layer ethanol concentrated filtrate and then distilled water is added with volume ratio is 1:1 and it would be separated into a second upper layer aqueous solution and a second lower layer precipitate after mixing and being placed at 6° C. overnight; Final, to perform fragmenting, spray drying at 40° C., and grinding to obtain α-Xones Prime, wherein the α-Xones Prime containing at least 50% of xanthone (based on the total content of α-mangostin and γ-mangostin) and the percent yield is 10% to the initial weight of mangosteen pericarp.

Example 3

To obtain fragment of mangosteen pericarp by drying and fragmenting the mangosteen pericarp and then the fragment is divided and packaged to a food grade of stainless-steel filter bucket. The fragment of mangosteen pericarp is soaked in chloroform with the ratio of weight to volume of 1:5 and the concentration of 70% and is placed at room temperature overnight and then to perform filtering to obtain a mangosteen pericarp chloroform extract. Next, the fragment of mangosteen pericarp is soaked in distilled water with ratio of weight to volume of 1:20 and is placed at room temperature overnight after heating at 95° C. for two hours; mangosteen pericarp water extract and mangosteen pericarp residue both be isolated by filter, and then α-Xones Prebio can be generated by spray drying and grinding the mangosteen pericarp residue at 40 to 60° C. Next, to concentrate the mangosteen pericarp chloroform extract and the mangosteen pericarp water extract to obtain a mangosteen pericarp chloroform concentrate and a mangosteen pericarp water concentrate, and then spray drying the mangosteen pericarp chloroform concentrate to obtain α-Xones Extract, wherein the α-Xones Extract containing about 10% of xanthone (based on the total content of α-mangostin and γ-mangostin) and the percent yield is 80% to the initial weight of mangosteen pericarp. Moreover, to add amount of formic acid into the mangosteen pericarp chloroform concentrate and it would be separated into a first upper layer aqueous solution and a first lower layer precipitate after homogenizing and being placed at room temperature for a while; then, to isolate the first upper layer aqueous solution and to add amount of ethanol with ratio of weight to volume of 1:1.2 to dissolve the first lower layer precipitate, and be filtered to obtain a mangosteen pericarp chloroform filtrate; and then α-Xones Aqua Choice can be obtained by spray drying the mangosteen pericarp aqueous solution concentrate and the first upper layer aqueous solution, wherein the α-Xones Aqua Choice containing about 3% of mangosteen water-soluble polyphenol and the percent yield is 15% to the initial weight of mangosteen pericarp. Moreover, N-hexane is added with volume ratio is 1:10 into the mangosteen pericarp chloroform filtrate and it would be separated into an upper layer alkane solvent and a lower layer chloroform filtrate after is mixed by vortex mixer to suspension state and being placed at room temperature for a while; the lower layer chloroform filtrate is heated in water bath at 45 to 50° C. and the is concentrated to obtaining a lower layer chloroform concentrated filtrate and then distilled water is added with volume ratio is 2:1 and it would be separated into a second upper layer aqueous solution and a second lower layer precipitate after mixing and being placed at 6° C. overnight; Final, to perform fragmenting, spray drying at 40° C., and grinding to obtain α-Xones Prime, wherein the α-Xones Prime containing at least 50% of xanthone (based on the total content of α-mangostin and γ-mangostin) and the percent yield is 10% to the initial weight of mangosteen pericarp.

Component Analysis of the Extract

Please refer to the FIGURE which shows an analysis result of ratio of α-mangostin and γ-mangostin in the extract of the present invention. The analysis is conducted by high performance liquid chromatography (HPLC) analysis for the α-Xones Extract (low purity of the mangosteen pericarp extract containing 10% to 30% of xanthone) and α-Xones Prime (high purity of the mangosteen pericarp extract containing 50% of xanthone) which obtained from example 2. The experiment detail is shown, SUPELCO INC. reverse phase, Waters Spherisorb ODS-2, 5 μm. 250 mm×4.6 mm or similar columns; flow rate of mobile phase: 1 mL/min; mobile phase containing solution A which is 0.1% formic acid solution and solution B which is acetonitrile; wavelength is 250 to 260 nm; and the mobile phase gradient is adjusted as follows:

|  | Solution A | Solution B |
| --- | --- | --- |
| Starting | 35% | 65% |
| 25 minutes | 0% | 100% |
| 28 minutes | 35% | 65% |
| 30 minutes | 35% | 65% |

As shown in the FIGURE, two significant peaks representing α-mangostin and γ-mangostin. By comparing their absorbance signal or/and area for those two peaks, we can know that the percentage of α-mangostin and γ-mangostin is 65~75% and 10~15%. Therefore, the process for preparing mangosteen pericarp extract from present invention could obtain different kind with different content of mangosteen pericarp extract which including 65~75% of α-mangostin and 10~15% of γ-mangostin. Moreover, it could be represented by the ratio of α-mangostin and γ-mangostin which is 5~7.

In view of the above, after implementation of the present invention, the objective of providing a simple preparation steps to address efficiency issue and with advantage of having α-mangostin and γ-mangostin in the extract product from the rind of the mangosteen in the same preparation process can be successfully achieved. Moreover, the present invention has advantage of no need to have heating under reflux in extraction steps and the solvents which used are more safe and eco-friendly.

The description of comprise, have, include, contain, or another similar semantics has the non-exclusive meaning. For example, an element, structure, product, or device contain multi requirements are not limited in the list of the content, but include another inherent requirement of element, structure, product or device not explicitly listed in the content. In addition, the term "or" is inclusive meaning, and not exclusive meaning.

The present invention is disclosed by the preferred embodiment in the aforementioned description; however, it is contemplated for one skilled at the art that the embodiments are applied only for an illustration of the present invention rather than are interpreted as a limitation for the scope of the present invention. It should be noted that the various substantial alternation or replacement equivalent to these embodiments shall be considered as being covered within the scope of the present invention. Therefore, the protection scope of the present invention shall be defined by the claims.

What is claimed is:

1. A process for preparing a mangosteen pericarp ethanol extract consisting essentially of:
    a) drying and fragmenting a mangosteen pericarp to obtain a fragment of the mangosteen pericarp;
    b) soaking the fragment of the mangosteen pericarp in at least 70% ethanol to yield a mangosteen pericarp extract and holding it at room temperature;
    c) filtering the mangosteen pericarp extract to obtain a mangosteen pericarp organic solvent extract, wherein the ratio of the weight to volume of the fragment of mangosteen pericarp and the organic solvent is 1:2 to 1:20;
    d) soaking and heating the fragment of mangosteen pericarp organic solvent extract of step c) in an aqueous solution and holding it at room temperature;

e) filtering it to obtain a mangosteen pericarp aqueous extract and a mangosteen pericarp residue, wherein the ratio of the weight to volume of the fragment of mangosteen pericarp and the aqueous solution is 1:10 to 1:20;
f) concentrating the mangosteen pericarp organic solvent extract and the mangosteen pericarp aqueous extract to obtain a mangosteen pericarp organic solvent concentrate and a mangosteen pericarp aqueous concentrate;
g) adding the mangosteen pericarp organic solvent concentrate to an aqueous solution;
h) homogenizing it, holding it at room temperature;
i) separating it into a first upper layer aqueous solution and a first lower layer precipitate;
j) isolating the first upper layer aqueous solution and adding ethanol to dissolve the first lower layer precipitate;
k) obtaining a mangosteen pericarp ethanol extract by filtration;
l) adding alkane solvent with a volume ratio of 1:1 to 1:10 into the mangosteen pericarp ethanol extract and mixing it with a vortex mixer, holding it at room temperature;
m) separating it into an upper layer alkane solvent and a lower layer ethanol filtrate;
n) heating and concentrating the lower layer ethanol filtrate in water bath to obtain a lower layer ethanol concentrated filtrate;
o) adding and mixing aqueous solution with a volume ratio of 1:1 to 3:1 into the lower layer ethanol concentrated filtrate, holding it at low temperature;
p) separating it into a second upper layer aqueous solution and a second lower layer precipitate; and
q) fragmenting, air-lay drying and grinding the second lower layer precipitate to obtain the mangosteen pericarp ethanol extract.

* * * * *